United States Patent [19]

Leonard

[11] Patent Number: 5,449,679
[45] Date of Patent: Sep. 12, 1995

[54] PROCESS AND PRODUCTS FOR REDUCING BIOLOGICAL FLUID LEVELS OF A LIPID SOLUBLE WASTE

[76] Inventor: Robert J. Leonard, 4 Hutchins Cir., Lynnfield, Mass. 01940

[21] Appl. No.: 283,092

[22] Filed: Jul. 29, 1994

[51] Int. Cl.$^6$ .................. A61K 31/415; A61K 31/40
[52] U.S. Cl. .................. 514/310; 424/422; 424/424; 424/426; 604/19; 604/5; 514/824; 128/898
[58] Field of Search .............. 514/310, 824; 424/422, 424/424, 426; 604/4, 5, 6, 19; 128/898

[56] References Cited

U.S. PATENT DOCUMENTS

| | | | |
|---|---|---|---|
| 3,950,529 | 4/1976 | Fisher et al. | 424/273 |
| 4,244,945 | 1/1981 | Gupta | 424/243 |
| 4,385,732 | 5/1983 | Williams | 241/167 |
| 4,452,775 | 6/1983 | Kent | 424/19 |
| 4,532,129 | 7/1983 | Comi et al. | 424/94 |
| 4,748,024 | 5/1988 | Leonard | 424/489 |
| 4,758,569 | 7/1988 | Swindell | 514/254 |
| 4,812,441 | 3/1989 | Kawai et al. | 514/824 |
| 4,895,558 | 1/1990 | Cham | 604/4 |
| 4,940,055 | 7/1990 | Brown | 128/653 A |
| 5,110,595 | 5/1992 | Wang | 424/422 |
| 5,110,738 | 5/1992 | Takano et al. | 435/240.27 |
| 5,112,827 | 5/1992 | Saunders et al. | 514/263 |
| 5,128,318 | 7/1992 | Levine et al. | 514/2 |
| 5,192,264 | 3/1993 | Fossel | 604/4 |
| 5,196,324 | 3/1993 | Bumol et al. | 435/70.21 |
| 5,208,019 | 5/1993 | Hansson et al. | 424/85.5 |
| 5,281,738 | 1/1994 | Parker | 556/427 |
| 5,290,549 | 3/1994 | Garnick | 424/85.1 |

OTHER PUBLICATIONS

Anderson, F. D., et al., "Tissue Response to Bioerodible, Subcutaneous Drug Implants: A Possible Determinant of Drug Absorption Kinetics," Pharmaceutical Research, v. 10, No. 3, pp. 369–380, 1993.

Pataki, M. et al., "Endocytosis of Oxidized LDL and Reversibility of Migration Inhibition in Macrophage-Derived Foam Cells In Vitro—A Mechanism for Atherosclerosis Regression?" Atherosclerosis and Thrombosis, vol. 12, No. 8, pp. 936–944 Aug. 1992.

Stoudemire, J. B., et al., "Effects of Recombinant Human Macrophage Colony–Stimulating Factor on Plasma Cholesterol Levels," Blood, vol. 77, NO. 4, pp. 750–755 Feb. 15, 1991.

Levine, D. M., et al., "In vivo protection against endotoxin by plasma high density lipoprotein," Proc. Natl. Acad. Sci. USA vol. 90, pp. 12040–12044, Dec. 1993.

von Baeyer, H., et al., "Covalent coupling of nucleodides to low density lipoprotein (LDL) generates macrophage specific (drug)–carriers," Int'l Journal of Clinical Pharmacology, Therapy and Toxicology, vol. 31, No. 8, pp. 382–386, 1993.

Schultis, H. W., et al., "Preparation of Nucleoside–LDL–Conjugates for the Study of Cell-Selective Internalization: Stability Characteristics and Receptor Affinity," Eur. J. Clin. Chem. Biochem, vol. 29, pp. 665–674, 1991.

Aviram, M., et al., "Serotonin Increases Macrophage Uptake of Oxidized Low Density Lipoprotein," Eur. J. Clin. Chem. Clin. Biochem., vol. 30, pp. 55–61, 1992.

Ravi Subbiah, M. T., et al., "Antioxidant Potential of Specific Estrogens on Lipid Peroxidation," J. Clin. Endocrinology and tabolism, vol. 77, No. 4, pp. 1095–1097, 1993.

(List continued on next page.)

Primary Examiner—Arthur C. Prescott
Attorney, Agent, or Firm—Wolf, Greenfield & Sacks

[57] ABSTRACT

Methods and pharmaceutical compositions for reducing the biological fluid level of a lipid soluble waste in a subject are provided. The methods involve selecting a subject diagnosed as having a hyperlipidemia-associated condition and subcutaneously introducing into the subject a biodegradable implant containing a pro-inflammatory lipid that promotes formation of an angiogenic tissue capsule containing a plurality of foam cells. The pro-inflammatory lipid is delivered in an amount sufficient to attain a detectable reduction in the biological fluid level of the lipid soluble waste.

21 Claims, No Drawings

OTHER PUBLICATIONS

Kita, T., et al., "The Role of Oxidized Lipoproteins in the Pathogenesis of Atherosclerosis," Clinical and Experimental Pharmacology and Physiology, vol. 19, pp. 37–42, 1992.

Fuhrman, B., et al., "Proteins derived from platelet α granules modulate the uptake of oxidized low density lipoprotein by macrophages," Biochimica et Biophysica Acta, vol. 1127, pp. 15–21, 1992.

Vilella, E., et al., "Interaction of oxidized low density lipoproteins with both apo B, E and scavenger receptors. A model for its production in vitro," Clinica Chimica Acta, vol. 210, pp. 93–108, 1992.

Maziere, C., et al., "Estrogens inhibit copper and cell-mediated modification of low density lipoprotein," Atherosclerosis, vol. 89 pp. 175–182, 1991.

Reid, V. C., et al., "Toxicity of oxidised low density lipoprotein towards mouse peritoneal macrophages in vitro," Atherosclerosis, vol. 98, pp. 17–24, 1993.

Yamada, N., et al., "Role of Monocyte Colony-Stimulating Factor in Cell Generation," M–CSF and Atherosclerosis, pp. 240–244, 1992.

Ku, G., et al., "Induction of Interleukin a$\beta$ Expression from Human Peropheral Blood Monocyte–derived Macrophages by 9–Hydroxyoctadecadienoic Acid," Journal of Biological Chemistry, vol. 267, No. 20, pp. 14183–14188, 1992.

Zioncheck, T. F., et al., "Interaction of Recombinant Apolipoprotein(a) and Lipoprotein(a) with Macrophages," J. Clin. Invest., vol. 887, pp. 767–771, Mar. 1991.

Srinivasan, S. R., et al., "Proteoglycans, Lipoproteins, and Atherosclerosis," Hypercholesterolemia, Hypocholesterolemia, Hypertriglyceridemia, Plenum Press, New York, pp. 373–381, 1990.

Hara, S., et al., "Probucol Pretreatment Enhances the Chemotaxis of Mouse Peritoneal Macrophages," Arteriosclerosis and Thrombosis, vol. 12, No. 5, pp. 593–600, May 1992.

Goodman and Gilman's, The Pharmacological Basis of Therapeutics, 1990, Pergamon Press, Inc., pp. 874–876.

PROCESS AND PRODUCTS FOR REDUCING BIOLOGICAL FLUID LEVELS OF A LIPID SOLUBLE WASTE

FIELD OF THE INVENTION

This invention relates to methods and pharmaceutical compositions for reducing the concentration of a lipid soluble waste in situ. More specifically, the invention relates to methods for retarding the development of atherosclerosis in mammals by reducing serum levels of low density lipoprotein.

BACKGROUND OF THE INVENTION

An elevated level of plasma cholesterol in the form of low density lipoprotein is associated with an increased risk of atherosclerosis, one of the leading causes of death in the United States and western europe. It is generally accepted that reducing plasma cholesterol levels reduces the risk of atherosclerosis by reducing the extent of atherosclerotic plaque formation and may, in early stages of the disease, reverse plaque accumulation. Accordingly, individuals who are diagnosed as having hypercholesteremia (excessive plasma cholesterol) or a predisposition to hypercholesteremia, typically are advised to reduce their plasma cholesterol levels by dietary or pharmacological means. (See, e.g., *Goodman & Gilman's The Pharmacological Basis of Therapeutics*, 8th ed., Pergamon Press, N.Y., N.Y., pp. 874–896 (1990)).

Cholesterol is carried in the blood in the form of lipoprotein complexes such as very low density lipoprotein (VLDL), low density lipoprotein (LDL) and high density lipoprotein (HDL). LDL transports cholesterol from the blood to the subendothelial space of blood vessel walls. Within the subendothelial space, LDL is peroxidized into a modified form generally referred to as oxidized LDL. Peroxidation of LDL in the subendothelial space is believed to play a key role in atherogenesis due to excess uptake of the oxidized LDL by local macrophages and the concomitant transformation of the macrophages into foam cells. (Subbiah, M. T., et al., *J. Clin. Endocrinol. and Metab.* 77(4):1095–1097 (1993)). HDL protects against plaque formation and delays the onset of atherosclerotic symptoms by mediating the transport of cholesterol from the vessel wall to the liver in a process known as "reverse cholesterol transport", (See, e.g., U.S. Pat. No. 5,281,738, issued to Parker, R., et al., and references cited therein, the contents of which are incorporated herein by reference).

Numerous methods directed to reducing plasma LDL levels and/or increasing plasma HDL levels have been proposed for preventing atherosclerotic plaque formation and delaying the onset of atherosclerosis symptoms. In general, these methods involve daily administration of a pharmacological agent for reducing LDL levels or periodic plasma delipidation by means of a continuous flow filtration system (e.g., U.S. Pat. No. 4,895,558, issued to B. Cham, the contents of which are incorporated herein by reference).

Several types of pharmacological agents have been disclosed for reducing plasma LDL levels. In general, these agents act either by diminishing the production of lipoproteins or by enhancing the efficiency of their removal from plasma. Drugs that lower the concentration of plasma lipoproteins include inhibitors of HMG CoA (hydroxymethylglutaryl-CoA) reductase, the rate-controlling enzyme in the biosynthetic pathway of cholesterol. Exemplary HMG CoA reductase inhibitors include mevastatin, lovastatin, pravastatin and simvastatin. (see, e.g., *Goodman & Gilman's The Pharmacological Basis of Therapeutics*, supra., and references cited therein, and U.S. Pat. No. 5,278,171, the contents of which are incorporated herein by reference). Other agents that have met with varying degrees of success with respect to reducing plasma LDL levels include gemifibrozil, clofibrate, fenofibrate, cholestryamine, colestipol and nicotinic acid. (See, e.g., U.S. Pat. No. 5,112,827, issued to Saunders, Jr. et al., the contents of which are incorporated herein by reference, for a discussion of the mechanisms of action and undesirable side-effects associated with many of the foregoing agents).

Although methods utilizing at least some of the above-identified pharmacological agents and/or methods may favorably alter the LDL/HDL ratio in the plasma of hyperlipidemic patients, each of the foregoing methods requires substantial patient compliance, i.e., daily self-medication, to reap a therapeutic benefit. None of the above-identified references and/or patents disclose a method for treating a large population of subjects diagnosed as having a hyperlipidemia-associated condition, in which the therapeutic efficacy of the method is independent of patient compliance.

SUMMARY OF THE INVENTION

The invention overcomes these and other problems by providing methods and pharmaceutical compositions for reducing the biological fluid level of a lipid soluble waste such as LDL in a manner which is simple, inexpensive and amenable to treating millions of patients suffering from a hyperlipidemia-associated condition or a predisposition thereto. In particular, the invention provides methods and compositions for reducing the serum level of LDL in a subject having a hyperlipidemia-associated condition, such as coronary atherosclerosis, hyperlipidemias (e.g. , hypercholesterolemia) or a predisposition to at least one of the foregoing conditions.

According to one aspect of the invention, a method for reducing in a subject a biological fluid level of a lipid soluble waste is provided. The method involves selecting a subject diagnosed as having a hyperlipidemia-associated condition and subcutaneously introducing into the subject a biodegradable implant containing a pro-inflammatory lipid. The pro-inflammatory lipid promotes formation of an angiogenic tissue capsule containing a plurality of foam cells (e.g., macrophages) around the implant.

The invention embraces at least two classes of pro-inflammatory lipids: (1) lipids that chemotactically recruit monocytes to the vicinity of the implant, e.g., oxidized LDL, (preferably these lipids also are chemostatic for macrophages) and (2) lipids that enhance uptake by foam cell precursors (such as macrophages) of the lipid soluble waste (e.g., cholesterol, acetylated LDL, oxidized LDL). The pro-inflammatory lipids do not inhibit oxidation of LDL in situ. Exemplary pro-inflammatory lipids that do not inhibit oxidation of LDL in situ include norethindrone, progesterone and other non-benzene ring containing lipophilic lipids.

The results of human clinical trials (see the Examples) evidences the therapeutic utility of the invention with respect to reducing serum LDL levels and increasing serum HDL levels. These and other aspects of the invention as well as various advantages and utilities will be more apparent with reference to the detailed description of the preferred embodiments.

DETAILED DESCRIPTION OF THE INVENTION

The prior art reveals the problems inherent to daily administration of a pharmacological agent for reducing serum levels of a lipid soluble waste (e.g., LDL). The present invention overcomes these problems by providing a biodegradable implant which delivers an amount of a pro-inflammatory lipid sufficient to attain a detectable reduction in the biological fluid level of the lipid soluble waste. Thus, the invention advantageously provides a method for reducing the biological fluid level of a lipid soluble waste for which therapeutic efficacy is independent of patient compliance.

According to one aspect of the invention, a method for reducing in a subject a biological fluid level of a lipid soluble waste is provided. The method involves: (a) selecting a subject diagnosed as having a hyperlipidemia-associated condition and (b) subcutaneously introducing into the subject an implant containing a pro-inflammatory lipid that promotes formation of an angiogenic tissue capsule containing a plurality of foam cells around the implant. The implant contains an amount of pro-inflammatory lipid that is sufficient to attain a detectable reduction in the biological fluid level of the lipid soluble waste. Methods for determining the biological fluid level of the lipid soluble waste are known to the artisan of ordinary skill in the art without the need for undue experimentation and are illustrated in the Examples. The active ingredients of the invention can be delivered in virtually any implant. The most preferred implants are partially fused implants or totally fused implants. Such implants are disclosed in U.S. Pat. No. 5,039,660 (partially fused implant) and U.S. Pat. No. 4,748,024 (totally fused implant), the entire contents of which are incorporated herein by reference.

As used herein, "hyperlipidemia-associated condition" refers to a condition that is manifested by an elevated level (or a predisposition to an elevated level) of a lipid-soluble waste (defined below). Hyperlipidemia-associated conditions include, for example, coronary atherosclerosis and hyperlipidemias such as familial hypercholesterolemia and hyperbetalipoproteinemia. Familial hypercholesterolemia (caused by absent, deficient, or non-functional LDL receptors) is manifested by a dramatically elevated LDL cholesterol level (J. Goldstein and M. Brown, *Medical Clinics of North America* 66:335–362 (1982)). Accordingly, the diagnosis of cholesterolemia, as well as other hyperlipidemia-associated conditions can be made in accordance with standard procedures known in the art by measuring lipid soluble waste (e.g., LDL) in a biological fluid sample.

As used herein, "lipid soluble waste" refers to a lipid soluble molecule or complex which, when present at an elevated level in a biological fluid (e.g., serum, plasma, lymph fluid) precipitates or exacerbates an unhealthy medical condition (e.g., coronary atherosclerosis, hyperlipidemia). Lipid soluble wastes are endogenous wastes in the sense that they represent the naturally occurring lipids that are present in mammalian cells as a result of normal metabolic synthesis or degradation processes, i.e., lipid soluble wastes are present in the biological fluids of clinically normal subjects. The elevated level of the lipid soluble waste, rather than its mere presence, is indicative of the presence of or predisposition to the unhealthy medical condition. Exemplary lipid soluble wastes include low density lipoprotein ("LDL"), modified LDL("mLDL"), cholesterol and cholesterol esters. In a particularly preferred embodiment the biological fluid is serum or plasma and the lipid soluble waste is LDL.

Low density lipoprotein (LDL) is the major cholesterol-transporting vehicle in plasma. LDL consists of free and esterified cholesterol, phospholipids, triacylglycerol and apoprotein B (a high molecular weight protein which contains the recognition site for binding of LDL to its receptor (the "LDL receptor"). Modification of the apoprotein's lysine residues causes an increase in uptake by a receptor that specifically binds to the modified LDL. Exemplary modified LDLs and the receptors to which they bind are described Applicant's copending U.S. application Ser. No. 08/049,943, the contents of which are incorporated herein by reference.

"Modified LDL" refers to a low density lipoprotein (LDL) that specifically binds to a modified LDL receptor, i.e., modified LDLs have in common an epitope that is recognized by a modified LDL receptor. (See, e.g., U.S. Pat. No. 5,196,324 which describes epitopes that are common to acetylated LDL and oxidized LDL and which cross-react with monoclonal antibodies to these modified LDLs.) Modified LDLs include naturally-occurring molecules, as well as non-naturally-occurring molecules. Naturally-occurring modified LDLs include, for example, oxidized LDL and proteoglycan-LDL complex formed in situ. Non-naturally occurring modified LDL can be prepared in vitro from commercially obtained LDL (Bionetics Research Institute, Rockville, Md.) or from LDL isolated from human plasma (Roma, P., et al., *J. Lipid Res.* 33:819–829 (1992)). Exemplary modified LDLs include acetyl LDL ("acLDL"), oxidized LDL ("oxLDL"), proteoglycan-LDL complex ("PG-LDL"), fibronectin-LDL complex, aggregates of LDL, glycated-LDL and immunoglobulin-LDL complexes.

"Foam cell precursor" refers to a stem cell or a stem cell derivative, such as a promonocyte, a monocyte and a macrophage, as well as a smooth muscle cell, which is capable of transformation (by internalizing lipid) into a foam cell. In a particularly preferred embodiment, the foam cell precursor is a macrophage. Foam cell precursors express or can be stimulated to express receptors that are capable of specifically recognizing and binding to the modified LDLs. Exemplary modified LDL receptors include receptors which recognize and bind to a modified LDL (e.g., the acLDL or oxLDL receptor, also known as the "scavenger receptor") or to the Fc portion of an antibody associated with LDL. (See Steinbrecher, U., et al., *J. Biol. Chem.* 264(26):15216–15223 (1989), and references cited therein, the contents of which are incorporated herein by reference).

As used herein, "foam cell" refers to any of the above-identified foam cell precursors which have been stimulated to internalize an enhanced level of lipid or lipoprotein in comparison with a cell which has not been so stimulated. Foam cells can be morphologically identified. Thus, for example, foam cells appear larger than a normal macrophage but smaller than a giant cell, lack interdigitation pseudopodia and are loaded with lipid droplets to the apparent visual exclusion of reticulum and organelles. Typically, the lipid droplets are approximately one tenth the size of the cell nucleus.

As used herein, "biodegradable implant" refers to a biodegradable device that is suitable for implantation into a subcutaneous site of a mammal (i.e., the implant can be "subcutaneously introduced" into the subject). Although only a particular lipid carrier, pure cholesterol, has been described in the Examples, other carriers also are contemplated by the invention. For example, cholesterol acetate or cholesterol derivatives including cholesteryl esters such as cholesterol chloride may be substituted for pure cholesterol. Furthermore, sterol carriers other than cholesterol or bioerodable carriers with properties substantially equivalent to cholesterol and cholesterol derivatives in terms of size, lipophilicity, crystallinity, and melting point may be substituted. Other carriers that may be substituted also include certain fatty acids and neutral fats.

The active ingredients of the invention can be delivered in virtually any implants. The most preferred implants are partially fused implants or totally fused implants. Such implants are disclosed in U.S. Pat. No. 5,039,660 (partially fused implant) and U.S. Pat. No. 4,748,024 (totally fused implant), the entire contents of which are incorporated herein by reference. A totally fused implant is one wherein the component(s) of the implant are melted and recrystallized to form a homogeneous crystalline matrix of active ingredient or active ingredient and carrier. A partially fused implant is one in which one of the active ingredient or carrier is melted and recrystallized, with the other being homogeneously dispersed and captured within the crystalline matrix of the other. Virtually any nonpolymer, crystal forming material can be used in the formation of such implants. Lipids that form crystals such as certain fatty acids as well as sterols are suitable. Cholesterol, the active agent of choice, may itself be melted and recrystallized alone or together with excipients or other active ingredients in forming fused pellets. Polymer based systems including polylactic glycolic acid, silastic, peptide systems and the like also are suitable, as are compressed tablets, and pump based systems. Sustained release systems are well known in the art and applicant does not wish to be bound by the selection of any particular system or combination of ingredients, except for applicant's active ingredient. It further is desirable to exclude anti-inflammatories in that a robust inflammatory response with tissue capsule formation is desired.

Alternative forms of implants which are useful for delivering the active ingredient of the invention are described in U.S. Pat. Nos. 3,993,073; 3,993,072; 3,967,618; 3,948,262; 3,948,254; 3,944,064; 3,921,636; and 3,854,480, the entire contents of which patents are incorporated in their entirety herein by reference.

In a particularly preferred embodiment, the implant is small enough to be pushed into a subcutaneous space through the lumen of a trocar needle, thus obviating the need for an incision (see, e.g., the Examples and U.S. Pat. Nos. 4,244,949, 4,753,636, 4,748,949, 5,039,660 and 5,137,669, the contents of which are incorporated herein by reference). The implant also can be introduced into other locations according to standard practice.

The implant contains a pro-inflammatory lipid that is capable of inducing a localized inflammatory response. As used herein, a "pro-inflammatory lipid" refers to a lipid that promotes formation of an angiogenic tissue capsule (i.e., a highly vascularized tissue mass) containing a plurality of foam cells around the implant. The highly vascularized nature of the tissue capsule allows the systemic circulation to contact the (lipid-internalizing) foam cell precursors and foam cells, thereby facilitating the transport of lipid soluble waste from the systemic circulation into the cells).

The implant contains an amount of pro-inflammatory lipid that is sufficient to attain a detectable reduction in the biological fluid level of the lipid soluble waste. The amount of lipid soluble waste (e.g., LDL, LDL-cholesterol) in the biological fluid is determined in accordance with methods known to one of ordinary skill in the art (see, e.g., the Examples). A "detectable reduction" in the biological fluid level of the lipid soluble waste refers to a reduction that is statistically significant.

Although not intending to be bound by a particular theory, it is believed that the mechanism by which the plurality of foam cell precursors in the vicinity of the implant are transformed into the plurality of foam cells involves receptor-mediated movement of the lipid soluble waste from the biological fluid (e.g., the vasculature of the tissue capsule) into foam cell precursors via one or more modified LDL receptors. Such receptor-mediated internalization additionally may involve endocytosis of the lipid soluble waste.

Applicant's observations (see the Examples and discussion below) suggest that oxidation of LDL plays an important role in the transformation of macrophages into foam cells and are consistent with the hypothesis that lipophilic lipids that inhibit oxidation of LDL, also inhibit foam cell formation. Accordingly, the pro-inflammatory lipids of the invention do not inhibit oxidation of LDL. Methods for determining whether a particular pro-inflammatory lipid is capable of inhibiting oxidation of LDL are described in U.S. Ser. No. 08/049,943 and in C. Maziere et al., *Atherosclerosis* 89(2-3) :175–182 (1991).

Two classes of pro-inflammatory lipids are disclosed herein: (1) pro-inflammatory lipids that are chemotactic for circulating monocytes and (2) pro-inflammatory lipids that enhance uptake by the foam cell precursors of lipid soluble waste. The artisan of ordinary skill in the art will appreciate that the above-disclosed classes of pro-inflammatory lipids do not represent a mutually or otherwise exclusive list.

In a particularly preferred embodiment, the pro-inflammatory lipids of class (1) are also chemostatic for macrophages. The methods disclosed by S. Hara, et al., for determining the effects of probucol on macrophage chemotaxis are adapted to identify pro-inflammatory lipids or other molecules that are chemotactic for macrophages (*Artheroscler. Thromb.* 12(5):593–600 (1992)). Oxidized LDL has been reported to be chemotactic for circulating monocytes and chemostatic for macrophages. The chemotactic component of oxLDL is believed to be lysolecithin molecules that are generated during LDL oxidation and lipase hydrolysis.

Although not intending to be bound by a particular theory, Applicant believes that presentation by the biodegradable implant of the pro-inflammatory lipid in situ promotes formation of the tissue capsule, as part of an inflammatory response which involves chemotactically recruiting monocytes from the circulatory system. The inflammatory response also may involve macrophage chemotaxis (i.e., macrophage migration toward an inflammatory mediator such as a cytokine). It is believed that upon biodegradation of the implant, the pro-inflammatory lipid activates local histiocytes to release cytokines (e.g., tumor necrosis factor, interleukin-1 and -2, and/or various colony stimulating factors) which then feed back to the bone marrow to enlist monocytes to the vicinity of the implant, thereby augmenting the initial chemotactic response and providing sufficient numbers of macrophages to surround the implant (see also, e.g., Anderson, J. M., et al., *Pharma. Res.* 10(3):369-380 (1993), the contents of which are incorporated herein by reference). In the absence of a chemotactic response, it is unlikely that local histiocytes would be present in sufficient quantity to cover the entire surface of the implant. Monocyte chemotaxis is involved also in the initiation of atherosclerotic plaques, followed by maturation of the monocytes to macrophages in the subendothelial space and transformation of the macrophages into foam cells (see, e.g., S. Hara, et al., *Arterioscler. Thromb.* 12(5):593-600 (1992)).

Pro-inflammatory lipids that enhance uptake by the foam cell precursors of lipid soluble wastes include at least the following subclasses of molecules: (i) pro-inflammatory lipids that stimulate release by the foam cell precursors of proteoglycans and (ii) pro-inflammatory lipids that are agonists of modified LDL receptors.

Macrophages are stimulated by intracellular cholesterol to release proteoglycans into the extracellular matrix (see e.g., R. Owens, et al., *Atherosclerosis* 91(3):229-240 (1991), cholesterol-enriched macrophages obtained from atherosclerosis-susceptible pigeons produce proteoglycans ("PG") which bind to LDL). S. R. Srinivasan et al. have reported that proteoglycans associate with extracellular LDL to form PG-LDL complexes that enter macrophages by a mechanism involving scavenger receptor-mediated endocytosis (*Adv. Exp. Med. Biol.* 285:373-381 (1991)). Although not intending to be bound to a particular theory, it is believed that the pro-inflammatory lipids stimulate macrophage production of proteoglycans (PG) which then enhances macrophage uptake of lipid soluble wastes (e.g., LDL) by providing proteoglycans for complexation with LDL to form PG-LDL complexes. The PG-LDL complexes then are taken up by the macrophages in a process involving modified LDL receptor-mediated endocytosis. In view of the foregoing evidence, a particularly preferred implant of the invention further includes proteoglycans (and/or agents which stimulate foam cells to release proteoglycans) to facilitate uptake by the foam cell of newly formed PG-LDL complexes in the vicinity of the implant.

Cholesterol is an exemplary pro-inflammatory lipid that stimulates foam cell precursors to release proteoglycans (R. Owens, et al., supra. (1991)). In a preferred embodiment, the implant contains at least 85% cholesterol; more preferably, the implant contains at least 90% cholesterol. In a most preferred embodiment, the implant contains 100% cholesterol.

Following internalization of the lipoprotein, free cholesterol is released from the lipoprotein and is incorporated into the cell membrane or stored in the cell in esterified form. The accumulation of free cholesterol in the cell down-regulates LDL receptor activity. In contrast, the accumulation of free cholesterol in the cell has little or no effect on modified LDL receptor activity. (See Moulton, K., et al., *PNAS USA* 89:8102-8106 (1992) and references cited therein, and U.S. patent application Ser. No. 08/049,943, the contents of which are incorporated herein by reference).. Accordingly, cholesterol released in situ from the implant readily enters the macrophages surrounding the implant via a process that is believed to involve modified LDL receptor-mediated endocytosis.

Pro-inflammatory lipids that enhance uptake by foam cell precursors of lipid soluble waste further include modified LDL receptor agonists. It is believed that binding of the agonist to the receptor triggers secondary cellular events which stimulate transformation of the foam cell precursors into foam cells. Numerous agonists of the scavenger (acLDL) receptor (e.g., acetylated LDL (acLDL) and oxidized LDL (oxLDL) and methods for the identification of such agonists (formerly referred to as "stimulating ligands") are disclosed in U.S. patent application Ser. No. 08/049,943, the contents of which are incorporated herein by reference.

The implants of the invention include at least one pro-inflammatory lipid (e.g., cholesterol and norethindrone) and optionally, a non-lipophilic agent for enhancing uptake by the plurality of foam cell precursors of the lipid soluble waste. Exemplary non-lipophilic agents include serotonin, an insulin-like growth factor, a monocyte colony stimulating factor, a proteoglycan and proteins derived from platelet alpha granules, including platelet derived growth factor (PDGF) (See, e.g., M. Aviram, et al., "Serotonin increases macrophage uptake of oxidized low density lipoprotein", *Eur. J. Clin. Chem. Clin. Biochem.* 30(2):55-61 (1992); N. Yamada, et al., "Role of monocyte colony-stimulating factor in foam cell generation", *Proc. Soc. Exp. Biol. Med.* 200(2):20-244 (1992); B. Fuhrman, et al., "Proteins derived from platelet alpha granules modulate the uptake of oxidized low density lipoprotein by macrophages", *Biochim. Biophys. Acta* 1127(1):15-21 (1992)).

For example, Yamada, N., et al., (Proc. Soc. Exp. Biol. Med. 200(2):240-244 (1992)) report that treatment of macrophages in vitro with monocyte colony-stimulating factor ("M-CSF") enhances the uptake by the macrophages of oxLDL and acLDL by increasing the number of scavenger receptors for these modified LDLs. Yamada, N., et al. further report that the increased cholesterol uptake by M-CSF-treated macrophages in vitro, coupled with the enhanced excretion of cellular cholesterol and its transport to the liver via a reverse cholesterol transport system involving HDL, may represent the cellular mechanism for removing extracholesterol from the extracellular matrix. (See also, J. B. Stoudemire, et al., "Effects of recombinant human macrophage colony-stimulating factor on plasma cholesterol levels", *Blood* 77(4):750-755 (1991)).

According to another aspect of the invention, a biodegradable implant containing at least 85% cholesterol and preferably, at least 90% cholesterol, is provided. Optionally, the implant includes one or more additional biodegradable lipid materials, from which the implant can be formed by the artisan of ordinary skill in the art using processes known in the art, provided that the additional material is not anti-inflammatory. Such materials include cholesteryl acetate and other cholesteryl esters that contain fatty acids having between two and twenty-four carbons, such as lauric acid, myristic acid, palmitic acid, stearic acid, glucuronic acid). Exemplary biodegradable, lipid substances, as well as three exemplary processes by which one or more lipid substances can be formulated into a biocompatible/biodegradable implant, are disclosed in U.S. Pat. No. 4,748,024, issued to Lerner, R.; U.S. Pat. No. 5,110,595, issued to P. Wang; and U.S. Pat. No. 4,452,775, issued to J. Kent, the contents of which patents are incorporated herein by reference.

In addition to the active therapeutic ingredient, the implants of the invention can contain a variety of inert materials such as excipients. Excipients can impart satisfactory properties for processing, and manufacture, including diluents, binders and lubricants. They also can impart desired characteristics to the finished product such as strength, solubility, bioavailability and the like, e.g., bulking agents, waxes, polymers etc. See for example *Remington's Pharmaceutical Sciences,* 18th edition, A. Gennaro, ed., Mack Publishing Co., Easton, PA (1990). Examples include dicalcium phosphate, calcium sulfate, lactose, cellulose, kaolin, mannitol, sodium chloride, starch, hydroxypropyl-methylcellulose, carboxymethyl cellulose, polyvinyl-pyrrolidene, waxes, polyethylene glycol, gelatin, sugars, sodium alginate, amylose, stearic acid, magnesium stearate, colloidal silicon dioxide and the like. In a preferred embodiment, the implants further include a binding agent and/or a lubricating agent, provided that these additional agents also are biocompatible, biodegradable and not anti-inflammatory. Exemplary binding agents and lubricating agents which satisfy these criteria are disclosed in U.S. Pat. No. 4,452,775.

The invention is not limited to the particular embodiments disclosed in the Examples. Accordingly, a "candidate" implant which differs in composition from those disclosed herein can be formulated and analyzed in vivo for its ability to promote formation of an angiogenic tissue capsule containing a plurality of foam cells without undue experimentation. The analysis of such "candidate" implants is performed by, for example: (1) implanting the candidate implant into the subcutaneous site of an animal (e.g., Wantanabe rabbit) for a period of time (e.g., three to six months) over which one would expect capsule formation by the above-disclosed biodegradable cholesterol implants; (2) removing the candidate implant (including its surrounding capsule, if any) from the animal; and (3) analyzing the candidate implant and its surrounding capsule by, for example, scanning electron microscopy. Implants which promote the formation of an angiogenic tissue capsule containing a plurality of foam cells are selected for further analysis including, for example, determining serum LDL levels as a function of implantation time in the animal model.

The following non-limiting Examples illustrate representative utilities of the instant invention. The exact mechanism(s) by which the pro-inflammatory lipid promotes formation of an angiogenic tissue capsule containing a plurality of foam cells and reduces the biological fluid level of the lipid soluble waste is not known. However, the literature (discussed above) discloses a number of molecules (e.g., scavenger receptor agonists, proteoglycans) which are known to facilitate the transformation of foam cell precursors into foam cells in vivo and/or in vitro. This knowledge, coupled with Applicant's discovery of a correlation between the formation of an angiogenic tissue capsule (containing foam cells) and a reduction in the serum levels of LDL (Example 1), suggested to Applicant the methods disclosed herein for reducing biological fluid levels of a lipid soluble waste. Methods for selecting additional pro-inflammatory lipids that are useful for achieving the objects of the invention, as well as methods for selecting materials for forming the biodegradable implants that are used to deliver the pro-inflammatory lipids, also are described herein.

EXAMPLES

EXAMPLE 1

Applicant's discovery of a correlation between formation of an angiogenic tissue capsule (containing foam cells) and a reduction in plasma levels of LDL.

A. METHOD FOR PREPARING THE IMPLANTS OF THE INVENTION

The methods for making the exemplary implants of the invention were disclosed in U.S. Ser. No. 5,039,660 (partially fused implant) and U.S. Pat. No. 4,748,024 (totally fused implant), the entire contents of which are incorporated herein by reference. The particularly preferred embodiments of the methods for making an implant are provided herein.

1. Partially Fused Peptide Implant 85 grams of pharmaceutical grade, microionized norethindrone (provided by Diosynth, Inc. of Chicago Ill.) and 15 grams of pure, pharmaceutical grade cholesterol (provided by ICN Pharmaceuticals of Covina Calif.) were intimately mixed and dispensed into a fluorocarbon tube (purchased from Teflon-TFE, Norton Chemplast, Inc. of Wayne, N.J.). The tube has a fluorocarbon surface to avoid sticking. The powder was placed into the tube in an amount such that when dried, the remaining powder equaled approximately 2 millimeters in depth after the first compression phase (approximately 20 grams). The powder was added to the tube by placing the filter sheet at one end of the tube. Preferably the filter sheet is a porous polymer filter having a pore size of 10 microns. Such a filter is obtainable under the trade name Gelman Versapore, 10-micron, sold by Gelman Sciences Inc. of Ann Arbor Mich. A vacuum force was then applied across the filter sheet to suck the powder into the tube. The tube was plugged with a 3 millimeter piece of Teflon beading and the dry mixture was then compressed against the plug by hand, using a steel compression pin inserted into the end of the tube opposite the plug. The plugged end was held against a tabletop to prevent the plug from being expelled from the tube. The degree of compression corresponded to about 2200 p.s.i. for 3 seconds. Then the tube containing the compressed dry mixture was transferred on the pin to an oven preheated to 180° F. The tube was exposed to this environment for 30 seconds. The tube then was removed form the oven and compressed by hand at about 150 p.s.i. for about 6 seconds as the partially-melted material cooled and recrystallized to form a hardened pellet. The mixture was allowed to cool for an additional 3 minutes without any compression, and, finally, the plugs and pellets were ejected from the Teflon tubes. Upon cooling the fused material was pure white, implying the lack of degradation products. The pellet was resilient and could be filed and formed with a very gentle abrasive action. The preferred pellets of the invention contain between 85% and 100% cholesterol and between 0 and 15% of another pro-inflammatory lipid material or other non-anti-inflammatory agent. For example, the other non-anti-inflammatory agent can be any of the above-described agents which enhance reduction of the lipid soluble waste (e.g., oxLDL, proteoglycan). A particularly preferred pellet is approximately 2½ millimeters in diameter by 6 millimeters in length.

2. Totally Fused Peptide Implant

A powdered mixture of cholesterol and norethindrone was formed as described above in the production of partially-fused implants. Accurate dispensing of the starting materials can be achieved by forming a paste which is made from a powdered mixture of the starting materials and a liquid such as ethyl alcohol. The alcohol may be dried out of the starting materials after dispensing, utilizing, for example, a standard vacuum oven. By forming a paste, the material can be dispensed accurately from a standard, automated device such as a micropipeter. The paste can be manufactured to have the flow characteristics of ordinary toothpaste. For further details, see U.S. Pat. No. 4,892,734, issued to R. Leonard, the contents of which are incorporated herein by reference.

Two grams of this mixture of norethindrone and cholesterol were mixed with two milliliters of 100% laboratory grade ethyl alcohol using a spatula to form a paste. The paste, or thirty-five milligrams of the norethindrone and cholesterol powder, were then spread onto a Teflon (R) coated steel spatula. The stainless steel spatula was approximately 20 mm in length and 10 mm in width and was covered uniformly with a fine layer of Teflon (R) tape. The skin applied was about 0.5 mm in thickness. The paste, which was spread onto the spatula in a thickness of about 0.5 mm, was allowed to dry in a vacuum oven for 30 minutes at 60° C., before the melt step. The non-Teflon (R) coated side of the spatula then was brought into contact with a hot plate which was heated to approximately 500° F. A clear melt resulted which beaded up like mercury and rolled off the surface of the spatula was held at an angle about 45° to horizontal. The spatula was contacted with the hot plate for less than 10 seconds. Upon cooling the fused material was pure white, implying the lack of degradation products. The pellet was resilient and could be filed and formed with a very gentle abrasive action. The pellet was approximately 2½ millimeters in diameter by 6 millimeters in length.

B. PRECLINICAL TESTING

1. Implantation into rabbits

The pellets are implanted in the subject according to methods known to one of ordinary skill in the art. Briefly, Wantanabe Heritable Hyperlipidemic (WHHL) rabbits, a model for familial hypercholesteremia, each receive four norethindrone rods. The rods are placed subcutaneously in the flexor surface of the forearm by means of a sterilized, disposable implanter (Harmon Injector). Four or five rods contained a total of from approximately 135 mg to approximately 170 mg of norethindrone.

C. IMPLANTATION OF CHOLESTEROL/NORETHINDRONE PELLETS INTO A HUMAN

The pellets were implanted in the subject according to methods known to one of ordinary skill in the art. Briefly, thirty-five regularly menstruating, sterilized (tubal ligation), healthy females each received four norethindrone rods. The rods were placed subcutaneously in the flexor surface of the forearm by means of a sterilized, disposable implanter (Harmon Injector). Four or five rods containing approximately 135 mg or 170 mg, respectively, of norethindrone were introduced into the subject.

D. Methods for determining plasma levels of cholesterol, LDL, and HDL

Blood samples were isolated from subjects at the time of implantation (baseline), 6 months, and twelve months after implantation. Lipoprotein levels were measured using standard procedures known in the art. One such method involved measuring lipoprotein levels in plasma using a Roche COBAS FARA II clinical chemistry analyzer (Roach Diagnostics) according to manufacturer's directions. An enzymatic assay was used to measure total plasma cholesterol, HDL cholesterol, and LDL cholesterol and the results were analyzed using a Roche COBAS FARA II clinical chemistry analyzer or using an alternative method having comparable sensitivity.

E. CLINICAL TRIAL RESULTS

(1) Composite Results

Applicant has discovered that a reduction in serum LDL occurs following subcutaneous introduction into a subject of the NET implant. Serum levels were measured at 0 time (i.e., baseline), six months, twelve months and 18 months post implantation. The implants (together with the surrounding tissue capsule) were removed at preselected time points (e.g., 6, 12, 18 months) and subjected to scanning electron microscopy (SEM). The SEM results showed an angiogenic tissue capsule containing foam cells surrounding the implant. In contrast, SEM results obtained for EST (estrogen) implants recovered at selected time points (e.g., 6, 12, 18 months) post-implantation showed a non-angiogenic fibrous tissue capsule surrounding the implant. The fibrous capsule contained fibroblasts but no macrophages or foam cells. That the NET implant had undergone biodegradation was evident from the irregular surface contour of the recovered implant. No biodegradation was observed for the recovered EST implants.

The lipid profiles between baseline (pre-implant) and follow-up treatment were compared (TABLE 1). Many subjects in each group exhibited decreases in total cholesterol between baseline and six months, baseline and 12 months, and baseline and the last observation level. The mean cholesterol level decreased between baseline and 6-months, 12-months and the last observation in the 4- and 5-pellet groups.

In the four pellet group, the decrease in mean total cholesterol (24.5% mg/dl (13%)) from baseline to the last observation during follow-up was statistically significant ($p<0.01$). For the five-pellet group, the mean cholesterol level decreased from baseline to the last observation during follow-up by 20.5 mg/dl (11.1%). No significant changes in HDL levels were noted from baseline to last observation with a small mean decrease (0.5 mg/dl or 0.9%) in the four pellet group and a small mean increase (1.6 mg/dl or 2.8%) in the five pellet group. Accordingly, essentially all of the observed change in total cholesterol was due to a reduction in LDL levels, which fell 21.7 mg/dl (19.9%, $p<0.01$) in the four pellet group and 18.3 ng/dl (16.9%, $p<0.01$) in the five pellet group. If these mean values are converted to total cholesterol/HDL ratios, the observed changes in the mean ration were from 3.26 to 2.91 for the four pellet group and from 3.27 to 2.83 in the five pellet group. Thus, the changes in lipids appeared to be quite similar in the four pellet versus the five pellet groups and in the same positive (therapeutic) direction.

A decrease in total cholesterol of the magnitude observed and reported above with essentially no change in HDL is a highly favorable trend. These results are either consistent with or better than previous data that address lipid changes occurring during use of progestin-only contraceptives.

E. Summary

Studies in rhesus monkeys demonstrate that implants formed of 15% cholesterol and 85% estrogen ("EST implants") do not promote formation of an angiogenic tissue capsule that contains a plurality of foam cells.

The above-described human clinical trial studies demonstrate that implants formed of 15% cholesterol and 85% norethindrone ("NET" implants) do promote the formation of an angiogenic tissue capsule that contains a plurality of foam cells.

Although estrogen and norethindrone share structural similarity, these molecules differ in the presence (estrogen) or absence (norethindrone) of a benzene ring. Maziere et al. have reported that estradiol, estriol and estone inhibit the in vitro oxidation of LDL by $Cu2+$, monocyte-like cells or endothelial cells and have suggested that the inhibition of LDL oxidation by these steroids is related to the presence of a benzene ring (since progesterone, which lacks a benzene ring, does not inhibit the oxidation of LDL under identical conditions) (Atherosclerosis 89(2-3):175-182 (1991)). Accordingly, in a particularly preferred embodiment, the pro-inflammatory lipid of the invention is a lipophilic steroid that does not include a benzene ring.

EXAMPLE 2

A method for determining whether an implant can promote angiogenic tissue capsule formation.

A. INTRODUCTION to EXAMPLE 2

This experiment illustrates a method for determining whether an implant can promote angiogenic tissue capsule (containing foam cells) formation. Bio-degradable implants formed of either cholesterol or norethindrone are tested for their ability to promote formation of an angiogenic tissue capsule containing foam cells as follows: First, an implant containing 100% cholesterol (a "100% CHO implant") or 100% norethindrone ("100% NET implant") is prepared in accordance with, for example, the process disclosed in U.S. Pat. No. 4,748,024, the contents of which are incorporated herein by reference. Second, the 100% CHO implant and the 100% NET implant are subcutaneously implanted into separate animals in accordance with the standard procedures such as those disclosed herein. Implants formed of 15% cholesterol/85% norethindrone ("NET implant") and 15% cholesterol/85% estrogen ("EST implant") serve as the positive and negative controls, respectively. Third, the implant (and surrounding tissue capsule) is extracted from the animal at preselected time periods during which one would expect to find capsule formation (based upon observations of the time periods required for the NET implant to form a tissue capsule). Fourth, the extracted implant (and capsule) is analyzed by, for example, scanning electron microscopy to determine whether angiogenesis and/or foam cells are present in the tissue capsule. To determine whether a correlation exists for the above-described implants between angiogenic tissue capsule

TABLE 1

Comparison of Lipid Profiles (mg/dl) Between Baseline and Follow-up by Treatment Received

| Lipid | 4-Pellet | | | | 5-Pellet | | | |
|---|---|---|---|---|---|---|---|---|
| | Total[1] | Mean | (SD) | p-value[2] | Total[1] | Mean | (SD) | p-value[2] |
| Total Cholesterol | | | | | | | | |
| Baseline | 19 | 184.1 | (31.97) | | 20 | 185.2 | (22.32) | |
| 6-month | 16 | 163.4 | (29.86) | | is | 161.6 | (26.31) | |
| 12-month | 12 | 168.9 | (30.57) | | 18 | 166.2 | (24.21) | |
| Last observation during follow-up | 17 | 162.2 | (31.05) | | 20 | 164.7 | (23.48) | |
| Baseline to 6-month change | 16 | −23.6 | (20.36) | <.01 | 19 | −23.4 | (18.90) | <.01 |
| Baseline to 12-month change | 12 | −25.8 | (22.88) | <.01 | 18 | −19.2 | (23.42) | <.01 |
| Baseline to last observation change | 17 | −24.5 | (20.22) | <.01 | 20 | −20.5 | (22.74) | <.01 |
| HDL | | | | | | | | |
| Baseline | 19 | 56.5 | (09.84) | | 20 | 56.6 | (11.31) | |
| 6-month | 16 | 55.9 | (11.46) | | 19 | 56.5 | (11.18) | |
| 12-month | 12 | 55.2 | (15.32) | | 18 | 58.3 | (13.00) | |
| Last observation during follow-up | 17 | 55.8 | (13.00) | | 20 | 58.2 | (12.62) | |
| Baseline to 6-month change | 16 | −1.0 | (09.99) | .69 | 19 | −0.4 | (05.44) | .82 |
| Baseline to 12-month change | 12 | 0.0 | (12.91) | .56 | 18 | 2.1 | (07.43) | .26 |
| Baseline to last observation change | 17 | −0.5 | (10.90) | 3 2 | 20 | 1.6 | (07.18) | .65 |

[1] For each time period, total is the number of subjects with data.
[2] Comparisons are made between baseline and each follow-up period within each treatment group using a paired t-test. No comparisons are made between treatment groups.
[2] Comparisons are made between baseline and each follow-up period within each treatment group using a paried t-test except where the assumption of normality was violated. The Wilcoxon signed rank test was used for HDL comparisons for the baseline to 12-month change and baseline to last observation change in the 4-Pellet group and for the baseline to 6-month change and baseline to last observation change in the 5-Pelet group. No comparisons are made between treatment groups.

(with foam cell) formation and reduced serum LDL levels, the foregoing experiment is modified such that the animal in which the implant is introduced is selected for having a hyperlipidemia-associated condition (such as homozygous Wantanabe heritable hyperlipidemic rabbits, an animal model of human familial hypercholesterolemia, or rabbits in which atherosclerotic lesions have been induced by dietary hypercholesterolemia (see, e.g., Maziere et al., (1991) supra. and references cited therein, the contents of which are incorporated herein by reference). The experiment further includes the step of determining the serum level of LDL prior to implantation and at various time periods post-implantation. Determination of the serum level of LDL is performed as described above. The implants are subcutaneously introduced into animals for preclinical testing and into humans for clinical testing as described above.

Preliminary experiments in which CHO implants or NET implants were implanted into Wantanabe rabbits having a hyperlipidemia-associated condition indicate that each of these implants resulted in a significant reduction (15–20%) in plasma LDL levels as early as one month following introduction of the implant into the animal.

Each of the above-identified patents and publications is incorporated in its entirety herein by reference.

Those skilled in the art will be able to ascertain, using no more than routine experimentation, many equivalents of the specific embodiments of the invention described herein. These and all other equivalents are intended to be encompassed by the following claims.

What is claimed is:

1. A method for reducing in a subject a biological fluid level of a lipid soluble waste, the method comprising:
   (a) selecting a subject diagnosed as having a hyperlipidemia-associated condition; and
   (b) subcutaneously introducing into the subject a biodegradable implant containing a pro-inflammatory lipid that promotes formation of an angiogenic tissue capsule containing a plurality of foam cells around the implant, wherein the pro-inflammatory lipid is delivered in an amount sufficient to attain a detectable reduction in the biological fluid level of the lipid soluble waste.

2. The method of claim 1, wherein the hyperlipidemia-associated condition is selected from the group consisting of coronary atherosclerosis, a predisposition to coronary atherosclerosis, hyperlipidemia, and a predisposition to hyperlipidemia.

3. The method of claim 1, wherein the lipid soluble waste is selected from the group consisting of a LDL, a modified LDL, cholesterol, and a cholesterol ester.

4. The method of claim 3, wherein the lipid soluble waste comprises LDL.

5. The method of claim 4, wherein the modified LDL is selected from the group consisting of an acetyl LDL, an oxidized LDL, a proteoglycan-LDL complex, a fibronectin-LDL complex, an aggregate of LDL, a glycated-LDL and an immunoglobulin-LDL complex.

6. The method of claim 1, wherein the plurality of foam cells are formed from a plurality of foam cell precursors selected from the group consisting of a monocyte, a macrophage and a smooth muscle cell.

7. The method of claim 6, wherein the foam cell precursor comprises a macrophage.

8. The method of claim 1, wherein the pro-inflammatory lipid is chemotactic for circulating monocytes and is chemostatic for macrophages.

9. The method of claim 8, wherein the pro-inflammatory lipid is oxidized LDL.

10. The method of claim 1, wherein the plurality of foam cells are formed from a plurality of foam cell precursors and wherein the pro-inflammatory lipid enhances uptake by the plurality of foam cell precursors of the lipid soluble waste to form the plurality of foam cells.

11. The method of claim 10, wherein the pro-inflammatory lipid stimulates release by the plurality of foam cells of a proteoglycan.

12. The method of claim 11, wherein the pro-inflammatory lipid comprises cholesterol.

13. The method of claim 10, wherein the foam cell precursors contain a receptor that binds to the lipid soluble waste and wherein the pro-inflammatory lipid comprises an agonist of the receptor.

14. The method of claim 13, wherein the agonist is selected from the group consisting of acetylated LDL and oxidized LDL.

15. The method of claim 1, wherein the pro-inflammatory lipid comprises a lipophilic steroid that does not inhibit oxidation of LDL.

16. The method of claim 15, wherein the lipophilic steroid is selected from the group consisting of norethindrone and progesterone.

17. The method of claim 16, wherein the lipophilic steroid comprises norethindrone.

18. The method of claim 1, wherein the implant includes at least two pro-inflammatory lipids.

19. The method of claim 18, wherein the pro-inflammatory lipids comprise cholesterol and norethindrone.

20. A biodegradable implant for delivering cholesterol in situ, comprising at least 90% cholesterol.

21. A biodegradable implant for reducing the level of a lipid soluble waste in a subject, comprising:
   (A) a pro-inflammatory lipid that promotes formation of an angiogenic tissue capsule containing a plurality of foam cells around the implant, wherein the plurality of foam cells are formed from a plurality of foam cell precursors; and
   (B) an agent for enhancing uptake by the plurality of foam cell precursors of the lipid soluble waste, wherein the implant contains an amount of the pro-inflammatory lipid sufficient to attain a detectable reduction in the biological fluid level of the lipid soluble waste when the implant is introduced into the subject.

* * * * *